United States Patent [19]

Tharrat et al.

[11] Patent Number: 4,466,431

[45] Date of Patent: Aug. 21, 1984

[54] DRESSINGS, MANUFACTURE AND USE

[75] Inventors: John Tharrat; Sally-Jane Harlock, both of Hull, England

[73] Assignee: Smith and Nephew Associated Companies Limited, England

[21] Appl. No.: 376,161

[22] Filed: May 7, 1982

[30] Foreign Application Priority Data

May 9, 1981 [GB] United Kingdom ............... 8114239
Jun. 24, 1981 [GB] United Kingdom ............... 8119490
Sep. 8, 1981 [GB] United Kingdom ............... 8127164

[51] Int. Cl.³ ........................................... A61L 15/00
[52] U.S. Cl. ............................... 128/156; 128/155; 604/304; 604/897
[58] Field of Search ............... 128/155, 156; 604/304, 604/306, 307, 308, 897

[56] References Cited

U.S. PATENT DOCUMENTS

| 1,967,923 | 6/1934 | Connolly | 128/155 |
| 2,693,438 | 11/1954 | Ward | 128/155 |
| 3,328,259 | 6/1967 | Anderson | 128/156 |
| 3,348,905 | 5/1964 | Reveley | 128/156 |
| 4,113,851 | 9/1978 | Lereen et al. | 128/156 |
| 4,143,655 | 3/1979 | Custer et al. | 128/90 |
| 4,310,509 | 1/1982 | Berglund et al. | 604/307 |
| 4,340,043 | 7/1982 | Seymour | 604/307 |

Primary Examiner—C. Fred Rosenbaum
Assistant Examiner—Harrie S. Samaras
Attorney, Agent, or Firm—Jacobs & Jacobs

[57] ABSTRACT

A dressing which comprises an ointment impregnated open-work support, having a protector on at least one face thereof characterized in that the protector is a film soluble in water, materials therefor and the manufacture thereof are described.

15 Claims, No Drawings

DRESSINGS, MANUFACTURE AND USE

The present invention relates to dressings suitable for application to wounds, materials therefore and the manufacture thereof.

Dressings consisting of an ointment impregnated open-work support such as tulle gras (sometimes called petrolatum gauzes) have been used for many years for dressing wounds. A soft paraffin tulle gras is disclosed in German Offenlegeschrift No. 2805248. Conventionally tulle gras are provided in sterile pouches. The tulle gras are prevented from adhering to the walls of the pouch (or to each other if more than one is packed in a pouch) by sheets of paper. When the gras is removed from the pouch the sheets of paper are pulled from the petrolatum and the gras placed on the wound. Occasionally this procedure results in the loss of petrolatum and if the gras is medicated then loss of medicament can also occur. Clearly it would be desirable to be able to avoid the use of paper or like material to protect the gras and like ointment impregnated open-work support dressings. It has now been discovered that soluble films may be employed that obviate the need to remove the protector.

Accordingly the present invention provides a dressing which comprises an ointment impregnated open-work support having a protector on at least one face thereof, characterised in that the protector is a film soluble in water.

Suitable ointment impregnated open work supports can include any of those conventionally used in impregnated gauze dressings of the art. Such dressings can employ a hydrophobic or non-water containing hydrophilic ointment.

Preferred ointment impregnated open-work supports are known as tulle gras as hereinbefore mentioned. Suitably the tulle gras dressing of the invention can comprise a gauze for example a leno gauze impregnated with a petroleum based ointment. Normally the petroleum based ointment will be a white or yellow petroleum jelly of a pharmaceutical grade optionally containing other ingredients for example a surfactant. Petroleum based ointments consisting of mixtures of soft paraffin and wool fat are also suitable.

Preferably the dressing is a sterile dressing. Aptly the sterile dressing is within a bacteria-proof pack, for example, a pouch. Suitable packs and sterilising procedures are described hereinafter.

In another aspect the invention provides a sterile dressing which comprises a tulle gras, a protector on at least one face of the tulle gras and a pouch enclosing the tulle gras and protector; characterised in that the protector is a film soluble in water.

For use the pouch may be opened and the tulle gras with protector removed and placed on the wound. The protector can then dissolve in the fluid released from the wound and its environment and the tulle gras is then free to fulfill its conventional function.

Most aptly both faces of the tulle gras are provided with a protector in the form of film soluble in water.

The film may be composed of any pharmaceutically acceptable water soluble material such as polyvinyl alcohol, methyl cellulose, ethyl cellulose, hydroxypropylcellulose, sodium carboxymethylcellulose, polyvinyl pyrrolidone, alginates and the like or mixtures thereof.

Most suitably the film is composed of polyvinyl alcohol. When used herein the term polyvinyl alcohol includes polyvinyl alcohol and partially acetylated polyvinyl alcohol. Most favourably this film is composed of polyvinyl alcohol in which 10% to 33% of the hydroxyl groups are acetylated, preferably 15% to 25% of the hydroxyl groups are acetylated and 10% to 22% of the hydroxyl groups are acetylated.

Aptly the polyvinyl alcohol employed in this invention has a molecular weight of from 15,000 to 120,000 more suitably from 20,000 to 100,000 and preferably from 25,000 to 85,000.

A favoured polyvinyl alcohol is Gohsenol GLO5 made by Nippon Gohsei and available from British Traders and Shippers Limited. Gohsenol GLO5 has a molecular weight of 30,000 and a degree of hydrolysis of 87% to 89%.

The water soluble film will generally contain from 1 to 50% of plasticizer, more usually from 5 to 40% of plasticizer, favourably from 8 to 30% of plasticizer and preferably from 10 to 25% of plasticizer.

The plasticizer employed in the film will normally be water, an alcohol or mixture thereof. Frequently the film will contain up to 25% water, more usually 1 to 20% water and commonly 2 to 10% water. The alcohol employed will usually be a di- or trihydroxylic compound such as ethylene glycol, propylene glycol, tetramethylene glycol, glycerol or the like. Favoured alcohols include propylene glycol and glycerol of which glycerol is normally preferred. Frequently the film will contain 1 to 25% of the alcohol, more usually 1 to 20% of the alcohol and favourably 8 to 15% of the alcohol.

Suitable water soluble films for use as a protector on dressings of the invention can have a weight per unit area of 10 to 125 g/m$^2$ and preferably a weight per unit area of 15 to 50 g/m$^2$. The water soluble film can be a film of substantially uniform thickness or a film of thinner areas. Suitably such films can have a thickness of 10 to 125 microns and preferably a thickness of 12.5 to 50 microns.

A favoured water soluble film is a polyvinyl alcohol (Gohsenol GLO5) film of approximately 25 micron thickness containing 5 to 15% by weight of a glycerol plasticizer.

Advantageously the water soluble film can have thinner areas to aid dispersal of the film in water. Such thinner areas are preferably in the form of recesses arranged in a uniform pattern on one or both surfaces of the film. Suitable recesses include grooves, which may be interconnected, for example intersecting sets of straight parallel grooves and depressions, which may be discrete, of for example triangular, rectangular, circular or a like geometric shape.

An apt water soluble film having thinner areas is a polyvinyl alcohol film which is known as Hi-Selon C type film manufactured by Nippon Gohsei and supplied by British Traders and Shippers Limited. Hi-Selon C type film is an embossed film of a water soluble polyvinyl alcohol with a degree of hydrolysis of 87% to 89% and a molecular weight of 44,000 to 72,000. The film is plasticized with a humectant type plasticizer such as polyethylene glycol and has an equilibrium moisture content of 8% to 10% at 20° C. and 65% relative humidity. Hi-Selon C type film has an embossed pattern of approximately 16 per cm parallel straight grooves in both the longitudinal and transverse directions which intersect at an angle of 90° to form a square grid pattern.

Favoured water soluble film having thinner areas are polyvinyl alcohol (Gohsenol GLO5) films of weight per unit area of 20 to 50 g/m$^2$ containing 5 to 15% by weight of glycerol with a uniform pattern of triangular shaped depressions on one surface.

The ointment of a dressing of the invention can optionally contain a medicament. Suitable medicaments include silver sulphadiazine, chlorhexidine acetate and povidone iodine.

The medicament employed is normally a curative agent which is topically effective. One particular class of curative agents envisaged for use in this invention is the topically applicable anti-infective agents. Such agents include chlorhexidine salts such as the gluconate, acetate, hydrochloride or the like; silver salts such as silver sulphadiazine; iodophors such as polyvinyl-pyrrolidone-iodone or the like; benzalkonium chloride or other topically acceptable antibacterial agent. Such agents also include fucidic acid salts such as the sodium salt; neomycin salts such as the sulphate or hydrochloride and other topically acceptable antibiotics.

It is preferred that the medicament is a powder. Suitable powders have a mean particle size of 1 micron to 500 microns and preferably have a mean particle size of 2 microns to 300 microns for example 5 microns to 250 microns.

Favoured povidone iodine powders are grades 30/06 and 17/12 manufactured by B.A.S.F. and presently available from Blagden Chemicals Limited.

Grade 30/06 has a mean particle size of 200 microns, average molecular weight of 40,000 and available $I_2$ content of 9% to 12%.

Grade 17/12 has a particle size of less than 150 microns, an average molecular weight of about 10,000 and an available $I_1$ content of 9% to 12%.

Povidone-Iodine powders of these grades with average particle sizes as low as 10 microns are also suitable.

A favoured chlorhexidine acetate powder has a mean particle size of 10 microns.

A favoured silver sulphadiazine powder has a mean particle size of 2 microns to 5 microns.

Normally the medicament will be present as 0.1% to 25% by weight of the ointment and usually as 0.4% to 15% by weight of the ointment.

In another aspect the invention provides a process of making a dressing of the invention which comprises placing a film soluble in water on one or both sides of an ointment impregnated open work support.

The ointment impregnated mesh fabric can be prepared in a conventional manner.

In a continuous process it is convenient to laminate a film soluble in water to one or both sides of an ointment impregnated open work support to form a continuous strip and to cut the strip into dressings of suitable size.

The sterile dressings of this invention may be prepared by placing a film soluble in water on one or both sides of the ointment impregnated open-work support for example a tulle gras, sealing the dressing into a bacteria proof pack such as a pouch and sterilizing the pouch and its contents.

Suitable water soluble polymer films can be made by hot melt extrusion or by casting the polymer onto a release surface or the like. Polyvinyl alcohol films can be conveniently made by casting a 4% to 35% by weight aqueous solution of the polymer in a conventional manner for example by means of a doctor blade over flat bed coating head onto a polyethylene coated paper and then drying in an oven at 85° C. A favoured polyethylene coated paper is known as Steralese 15 made by Sterling Coated Papers Limited.

Suitable water soluble films having thinner areas can be made by casting the polymer, as a solution or a hot melt, in contact with a surface having a pattern of raised areas. These films can also be made by embossing a film with a similar patterned surface.

An apt process of forming such films comprises casting an aqueous solution of polymer in contact with a sheet embossed with uniform pattern of raised areas.

A favoured process of forming a polyvinyl alcohol film with thinner areas comprises casting an aqueous solution of polyvinyl alcohol (30% by weight of Gohsenol GLO5) containing a plasticizer (5% to 15% by weight of glycerol) by means of a doctor blade over flat bed coating head onto a sheet embossed with a uniform pattern of raised triangles (polyethylene film type 04514 emboss code 14 available from AOE Plastics GmbH).

The pouches employed are most aptly made of paper or some other ethylene oxide permeable material as a favoured method of sterilization is by treatment with ethylene oxide in conventional manner. Alternatively the pouches can be made of a heat sealable aluminium foil laminate. Suitable heat sealable aluminium foil laminates for example a paper/aluminium foil/ethylene vinyl acetate/lacquer laminate are available from DRG Flexible Packaging Limited. Suitable sterilization methods for aluminium foil laminate pouches include gamma irradiation.

The use of a water soluble film protector on dressings of the invention which does not require removal avoids the loss of ointment incurred when a protector is removed from conventional dressing. This allows the open work support of dressings of the invention to be impregnated with a lower weight per unit area of ointment than that of conventional dressings (typically 250 g/m$^2$) without loss of dressing efficiency.

Suitably the open work support of dressings of the invention can be impregnated with a weight per unit area of 100 to 220 g/m$^2$ and preferably a weight per unit area of 120 to 200 g/m$^2$.

The following Examples illustrate the invention:

EXAMPLE 1

A 10 cm wide strip of Leno gauze impregnated with petroleum jelly was laid onto a 10 cm wide length of 20 microns thick polyvinyl alcohol film (Hi-Selon C type embossed film) and a further 10 cm wide length of polyvinyl alcohol film placed on top to form a laminate of impregnated gauze between two layers of film. The laminate strip was then cut into 10 cm × 10 cm dressings which were packed individually into sealed aluminium foil pouches and sterilized by gamma irradiation (2.5 megarads) in a conventional manner.

EXAMPLE 2

In a similar manner to example 1 a medicated tulle gras dressing of the invention was made by impregnating a Leno gauze with 150 to 200 g/m$^2$ of petroleum jelly B.P. containing 0.525% by weight of chlorhexidine acetate (micronised powder from ICI Pharmaceuticals Limited).

EXAMPLE 3

A 10 cm wide strip of Leno gauze impregnated with petroleum jelly B.P. (160 g/m$^2$) containing a surfactant (0.1% by weight of Tween 60) and povidone iodine powder (6% by weight of grade 30/06 available from Blagden Chemicals Limited) was laid onto a 10 cm wide strip of embossed polyvinyl alcohol film (24 gsm) and a similar strip of embossed polyvinyl alcohol film placed on top of the impregnated layer to form a laminate.

The embossed polyvinyl alcohol film was made by coating an aqueous solution (30% by weight) of Gohsenol GL05 containing glycerol (5% by weight) onto an embossed polyethylene film (Grade 04514, emboss code 14 available from AOE Plastics GmbH) by means of blade over flat bed coating head and drying the cast film in an oven at 70° to 80° C.

The laminate strip was then cut into 10 cm×10 cm dressings, packed individually into sealed aluminium foil pouches and sterilized by gamma irradiation (2.5 megarads) in a conventional manner.

The aluminium foil pouches were formed by edge heat sealing a front foil consisting of a bonded paper (40 gsm)/aluminium foil (24 gsm)/ethylene-vinyl acetate (23 gsm of Surlyn 1652) laminate and a back aluminium foil of similar construction coated with heat seal pealable lacquer (25 gsm) available from DRG. Flexible Packaging Limited.

WOUND HEALING STUDIES

The dressings of Example 3 were placed on partial thickness wounds (2.5 cm×2.5 cm) made on the backs of pigs (large white breed). It was found that the water soluble protectors of these dressings, in contact with the wound exudate, dissolved within 1.5 minutes. Examination of wound sections over a period of three months showed that the healing and pathology of the wounds were not substantially different from that of comparative test conventional tulle gras dressing (Jelonet made by T. J. Smith and Nephew Limited).

What we claim is:

1. A sterile dressing which comprises a hydrophobic or non-water containing hydrophilic ointment impregnated open-work support having a protector on both faces thereof, said protectors being films soluble in water.

2. A sterile dressing according to claim 1 in which the ointment impregnated open-work support is a tulle gras.

3. A sterile dressing according to claims 1 or 2 within a sealed bacteria proof pouch.

4. A sterile dressing according to claim 1 in which the films have thinner areas to aid the dispersal of the films in water.

5. A sterile dressing according to claim 1 in which the films have a weight per unit area of 15 to 50 g/m².

6. A dressing according to claim 1 in which the ointment contains a topically acceptible antibacterial agent.

7. A dressing according to claim 6 in which the antibacterial agent is present as 0.4% to 15% by weight of the ointment.

8. A dressing according to claim 1 in which the open-work support is impregnated with an ointment at a weight per unit area of 120 to 200 g/m².

9. A sterile dressing which comprises a tulle gras, a protector on both faces of the tulle gras and a pouch enclosing the tulle gras and protectors, said protectors being films soluble in water.

10. A dressing according to claim 9 in which the films are films of polyvinyl alcohol containing 10 to 22% acetylated hydroxyl groups.

11. A dressing according to claim 10 in which the polyvinyl alcohol contains 1 to 20% by weight of an alcohol plascticizer.

12. A dressing according to claim 9 in which the tulle gras contains a topically acceptible antibacterial agent.

13. A dressing according to claim 12 in which the antibacterial agent is a chlorhexidine salt.

14. A dressing according to claim 12 in which the antibacterial agent is polyvinyl pyrrolidone iodine.

15. A process for the production of the dressing of claim 9 which comprises placing a film soluble in water on both sides of the tulle gras, sealing the tulle gras with the films into a pouch and sterilizing the pouch and its contents.

* * * * *